United States Patent [19]

Patneau

[11] 3,990,442
[45] Nov. 9, 1976

[54] RESPIRATORY TREATMENT DEVICE

[76] Inventor: Robert A. Patneau, 2930 NE. 39th Court, Pompano Beach, Fla. 33304

[22] Filed: June 6, 1975

[21] Appl. No.: 584,618

[52] U.S. Cl. .............................. 128/194; 128/145.6
[51] Int. Cl.² ...................................... A61M 16/00
[58] Field of Search .......................... 128/192–201, 128/145.5–145.8, 142.3

[56] References Cited
UNITED STATES PATENTS

| | | | |
|---|---|---|---|
| 3,045,668 | 7/1962 | Lee | 128/145.5 |
| 3,172,406 | 3/1965 | Bird et al. | 128/194 |
| 3,580,249 | 5/1971 | Takaoka | 128/194 |
| 3,603,308 | 9/1971 | Spradling et al. | 128/194 |
| 3,842,828 | 10/1974 | Bird | 128/145.8 |
| 3,865,106 | 2/1975 | Palush | 128/145.8 |
| 3,893,458 | 7/1975 | Fletcher et al. | 128/145.8 |

Primary Examiner—Robert W. Michell
Assistant Examiner—Henry J. Recla
Attorney, Agent, or Firm—Malin & Haley

[57] ABSTRACT

A device for the treatment of pulmonary ailments including an intermittent constant pressure breathing apparatus which simultaneously provides both humidified air and a nebulized medicant through a single breathing tube. The device is characterized as being very compact and portable and is adaptable to several modes of operation, including supplying humidified air alone, providing nebulized medicant along, or simultaneously providing nebulized, humidified air and medicant. Various modes of operation may also include providing intermittent positive pressure breathing to a patient.

2 Claims, 4 Drawing Figures

RESPIRATORY TREATMENT DEVICE

BACKGROUND OF THE INVENTION

This invention relates generally to a device for treatment of respiratory ailments and specifically to a device for providing both nebulized medicants and humidified air to a patient suffering a respiratory ailment. Several respiratory diseases or ailments, such as emphysema, asthma, bronchitis, pulmonary fibrosis and other pulmonary and bronchial diseases are treated utilizing various respiratory apparatus which provide humidified air to the lungs of a patient or a nebulized medicant under pressure to the patient's lungs. These devices have been characterized in the past by being quite complicated in structure, expensive, bulky and not easily transportable.

The instant invention provides a very compact respiratory treatment device which provides both humidified air and a nebulized medicant simultaneously with or without intermittent positive pressure breathing in a single compact system which is readily transportable for use almost anywhere. The device includes a first air compressor with its output in fluid communication with an aerosol generator. The output of the aerosol generator provides nebulized, humidified air under positive pressure and is in fluid communication with a medicant nebulizer and mouthpiece. A second air compressor output is connected to a cycling valve for providing intermittent positive pressure breathing and to the medicant nebulizer, the nebulizer and a fluidic inverter cycling valve being coupled to a breathing mouthpiece. In this configuration, the device is capable of providing nebulized, humidified air from the aerosol generator and nebulized medicant from the nebulizer simultaneously, with a fluidic inverter cycling valve allowing for intermittent positive pressure breathing (IPPB) to the patient. Also it has been determined that the first air pressure source provides a slight back pressure which is advantageous for the patient during exhalation of air from the lungs.

BRIEF DESCRIPTION OF THE INVENTION

A device for the treatment of respiratory ailments which includes an intermittent positive pressure breathing (IPPB) apparatus, a positive pressure source of humidified air, and a nebulizer for nebulizing medicants with the humidified air source outlet being coupled through the nebulizer coupled to the IPPB apparatus. The device includes two air compressors, the first air compressor being in fluid communication with a fluidic cycling valve which is connected into a mouthpiece nozzle which is inserted into the mouth of the patient. The second air compressor delivers positive pressure air into an aerosol generator which is a conventional nebulizer and consists of a liquid receptacle having a baffling system which introduces droplets of liquid into the pressurized air. The liquid in the reservoir may be heated before being received in the receptacle. The outlet of the aerosol generator is connected to a nebulizing chamber in fluid communication with the mouthpiece. A branch conduit from the second positive pressure air source delivers pressurized air to the nebulizer chamber for nebulizing the medicant. The main line of the second air source is connected to a fluidic inverter cycling valve which controls and regulates the IPPB so that intermittent positive pressure breathing is accomplished. The delivery of humidified air with a nebulized medicant is accomplished by combining a fluidic inverter cycling valve known under the trade name "RETEC NC-30", part no. 3007 with a nebulizer known under the trade name "BIRD MICRONEBULIZER", part no. 158 by connecting the humidified air outlet as an input to the "bird" nebulizer, the output being coupled to the mouthpiece. The device is capable of operation in different modes with very slight modification which include providing (1) nebulized humidity to the patient, (2) humidified air only to the patient or (3) the nebulized medicant alone to the patient, each mode including intermittent positive pressure breathing, if necessary.

The two air compressors and the aerosol generator are mounted on a small rigid platform or base. The unit may be enclosed with a cover and handle for storage and portability. The mouthpiece, cycling valve and nebulizer and the associated flexible tubing may be stored with the unit.

To operate the device such that both humidified air and the nebulized medicant are simultaneously provided to the patient using IPPB, a medicant is placed in the nebulizer chamber which is then connected to the mouthpiece and the outlet conduit from the aerosol generator, which contains a saline solution for humidification. The high pressure air source is connected through the RETEC NC-30 fluidic cycling valve to the mouthpiece, with a bleed-off from the high pressure source being used and coupled into the "bird" nebulizer chamber which provides an air pressure source to nebulize the medicant. The device is then turned on and the patient places the mouthpiece in his mouth, receiving both humidified air and the nebulized medicant. The Applicant has also found that the utilization of two sources of air under pressure provides a positive back pressure during exhalation which is of therapeutic value to the patient. The system provides a positive pressure humidified and medicant nebulized air supply for the patient during breathing inspiration with flow turn off during expiration. The first and second air pressure sources are conventional electric air compressors with an upper operational limit of 25 psi and may include a moisture filter and pressure regulating valve which are conventional.

It is an object of this invention to provide a compact, portable respiratory unit which can provide both humidified air for intermittent positive pressure breathing simultaneously with a nebulized or atomized medicant.

It is another object of this invention to provide an improved respiratory apparatus which is non-complex in operation, has increased efficiency, can be constructed at reduced cost, and is portable.

But yet still another object of this invention is to provide an apparatus for treatment of pulmonary diseases which may be utilized to provide humidified air or oxygen and nebulized or atomized medication, either individually or simultaneously to a patient.

In accordance with these and other objects which will be apparent hereinafter, the instant invention will now be described with particular reference to the accompanying drawings.

PREFERRED EMBODIMENT OF THE INVENTION

Figure 1:
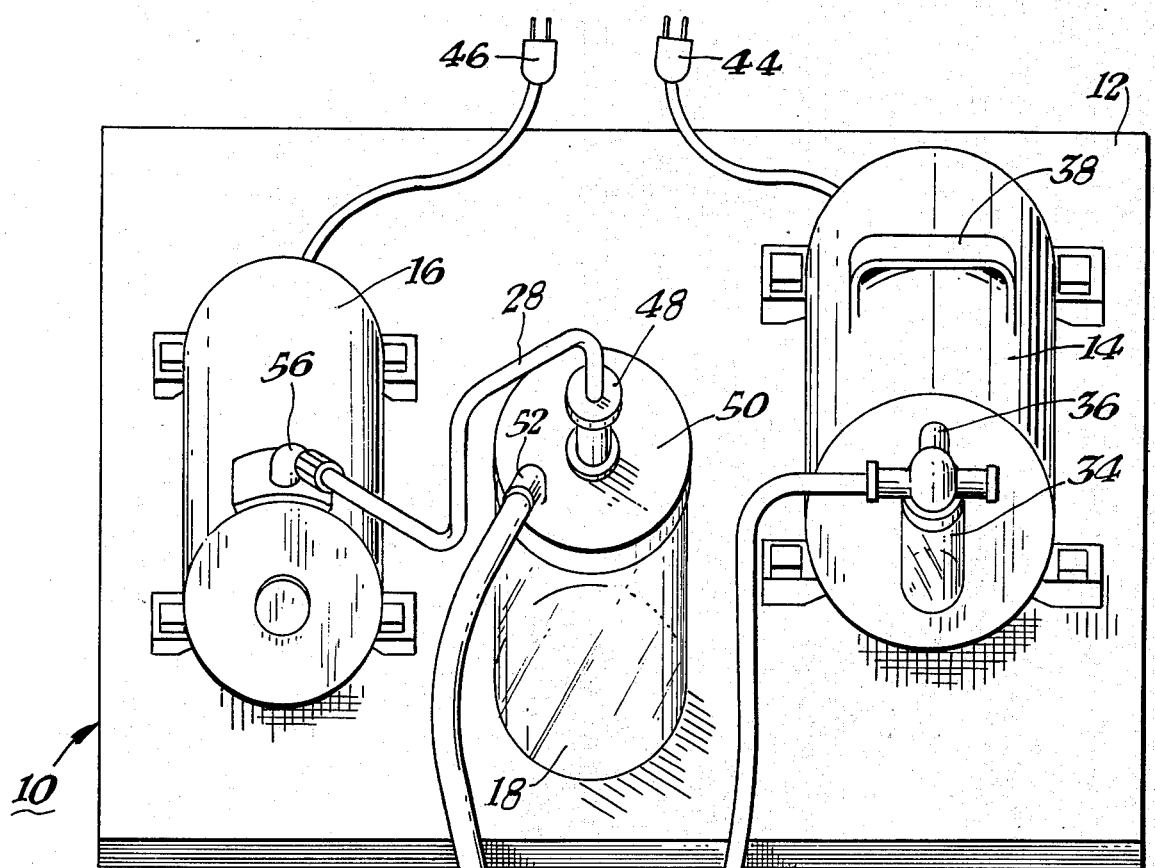
FIG. 1 shows a perspective view of the instant invention which is arranged to provide simultaneous humidified air under pressure and nebulized medication to the patient.

Referring now to the drawings and specifically FIG. 1, one embodiment of the instant invention is shown generally at 10 comprising a rigid mounting surface 12 to which is attached a source of pressurized air, an electrically actuated air compressor 16. Attached to the output of compressor 16 is a flexible conduit 28 which is received into aerosol generator 18 which contains a liquid (in most cases a saline solution) which is used to provide nebulized humidity to the air received from the compressor 16. The output of the aerosol generator is an outlet 52 which is coupled by flexible conduit 30 which may be of any particular length to the bird nebulizer 20. In an alternate embodiment, a "Hudson Updraft Manifold" Nebulizer, part no. 1408 could be substituted.

Another source of air under pressure is provided from a conventional air compressor 14 which includes a handle 38 disposed on its upper surface. The compressor 14 is attached to the base 12 by a plurality of screws. A vapor filter 34 is conventional and prevents vapor from being received into the air compressor 14. A pressure gage and control valve regulator is coupled to the compressor 14. The outlet 36 of the compressor 14 is coupled to a small diameter flexible tube 32 (the length of which may be varied) which is connected to inlet 42 of the cycling valve 22 which includes an internal conduit and handle portion 24. The RETEC NC-30 cycling valve 22 is coupled at its outlet side to a mouthpiece 26 which is adapted to be received into the mouth of a patient. The mouthpiece is also coupled to the output side of nebulizer 20 which receives air under pressure through conduit 40 which is connected at one end to a T-section at the inlet side 42 of the cycling valve 22. The outlet portion of flexible conduit 40 is connected to inlet conduit 54 which is received into the nebulizer 20.

The cycling valve 22 in the preferred embodiment is known under the trade name RETEC and it is known as a RETEC Model NC-30 fluidic cycling valve. The RETEC cycling valve is characterized by having no moving parts and allows for control of the air pressure being received in the mouthpiece by the patient. The valve actuates and controls the inhalation air flow and pressure which is necessary when providing intermittent positive pressure breathing to the patient. The nebulizer 20 into which a particular amount of medicant is inserted is, in this embodiment, known under the trade name as "BIRD MICRONEBULIZER" and is manufactured by the BIRD MANUFACTURING CO., part no. 1408.

The embodiment as shown in FIG. 1 is capable of providing both a nebulized medicant from liquid medicant contained in nebulizer 20 and humidified air from the aerosol generator 18. With a very simple modification of the hoses and mouthpiece 26, the device may be separately used to supply only nebulized medicant with the removal of hose 30. The unit may be used to provide humidified air from the aerosol apparatus 18 through hose 30 to mouthpiece 26 with or without the use of the IPPB through hose 32. The system itself has several overall modes of operation for accomplishing different types of treatment dependent upon the treatment necessitated by the particular patient. Thus, the system may be easily adapted to provide (1) humidified air under pressure, (2) humidified air at low pressure, (3) oxygen supplement, (4) nebulized medicant under pressure alone, (5) nebulized medicant under low pressure and as in the embodiment shown, (6) nebulized medicant in combination with humidified air. The patient may utilize a mouthpiece as shown or a noze and mouth cover dependent upon the particular treatment and patient.

During the exhalation phase of the operation when utilizing the IPPB, it is noted that the nebulizer 20 will still be receiving humidified air under positive pressure in mouthpiece 26 such that even during the exhalation phase by the patient, a slight pressure, will be present against which the patient must exhale. This provides additional therapy for the patient which forces him to exhale more deeply to overcome this slight back pressure resulting from the humidified air in the aerosol generator 18 received from compressor 16.

Figure 2:
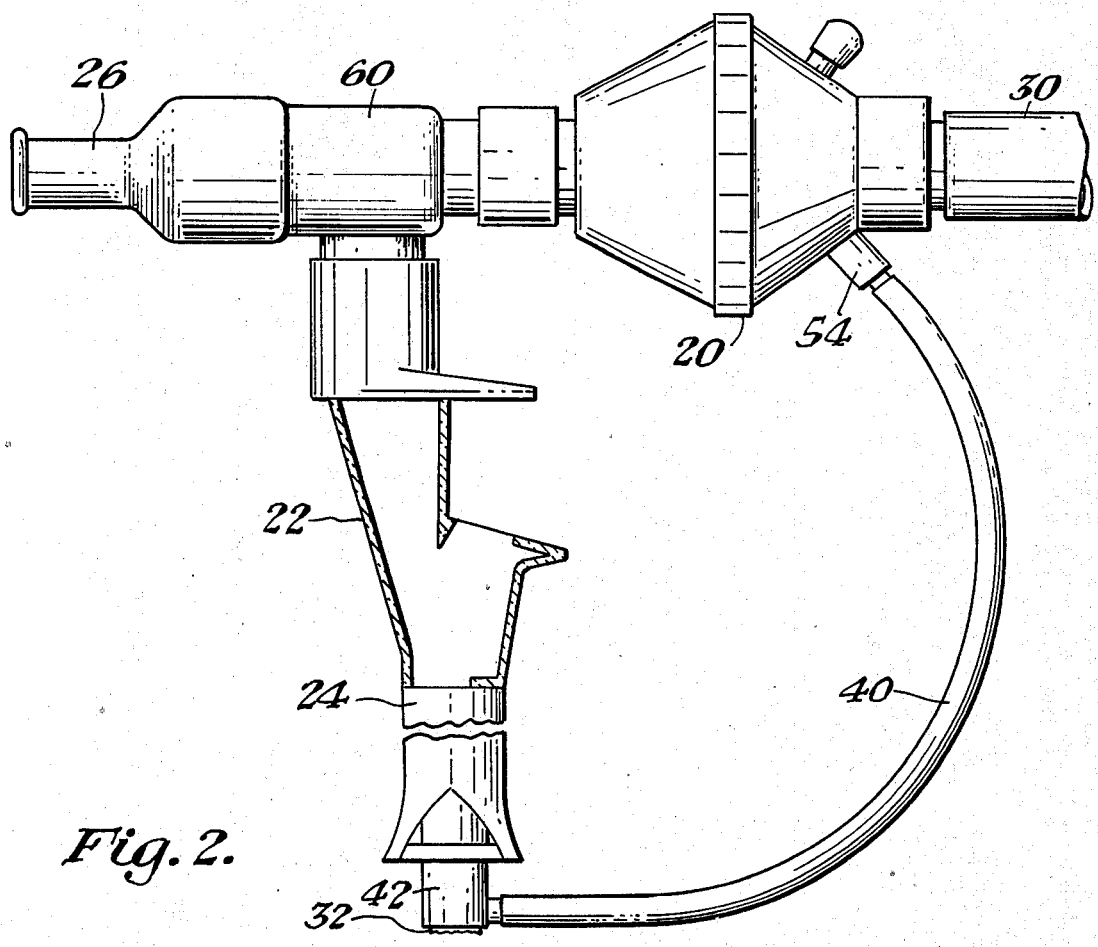
FIG. 2 is a side elevational view of the mouthpiece, cycling valve and nebulizer as utilized in the instant invention.

FIG. 2 shows the nebulizer, cycling valve and mouthpiece coupled to simultaneously provide aerosol or humidified air or gas in combination with the nebulized medicant. Air under pressure is received from hose 32 into T conduit 42 and flows into the cycling valve 22 and T-shaped conduit 60 which is connected at one end to the mouthpiece 26. The cycling valve 22 is the RETEC NC-30 model part no. 7003 and operates to provide and control the pressure from the air pressure source during the inhalation and exhalation cycle of the patient such that during exhalation the pressure source of air is shut off to allow the patient to exhale properly. A portion of the air flow is diverted through hose 40 into receiving conduit 54 in the bird medicant nebulizer 20. The air received through hose 40 is used to nebulize the medicant in nebulizer 20. A low pressure source of air is received into nebulizer 20 through hose 30 which introduces humidified air from the aerosol generator (not shown in FIG. 2) through the nebulizer 20 which is also received into conduit 60 and into mouthpiece 26. Within the nebulizer chamber 20 the medicant therein is also nebulized and thus mixed with the humidified air received in hose 30 such that both the humidified air and the nebulized medicant are received in the mouthpiece 26.

Figure 3:
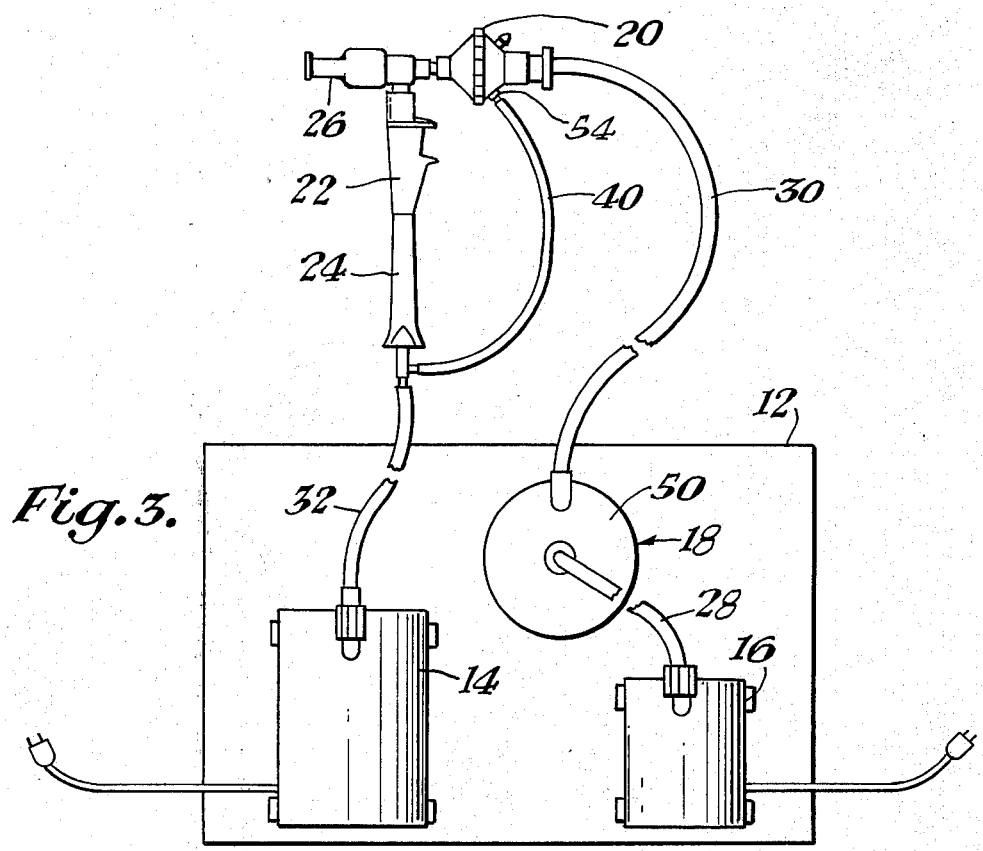
FIG. 3 is a top plan view of the instant invention including the cycling valve, nebulizer and mouthpiece attachment.

FIG. 3 shows a top view of the unit adapted for simultaneous nebulized medication and humidified air. The compactness and size of the unit is such that a box-like cover may be added to fit on the base 12 to which the aerosol generator 18 and the air compressors 14 and 16 are rigidly attached.

Figure 4:
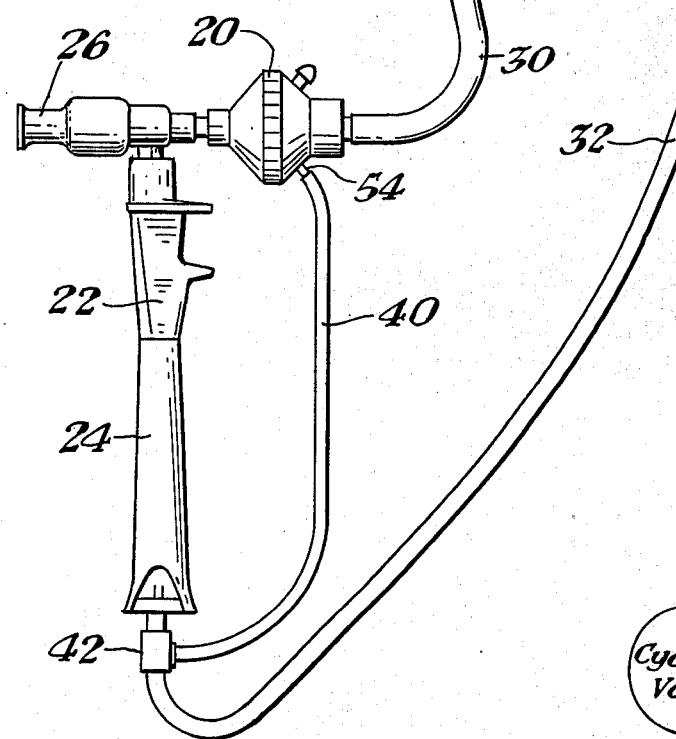
FIG. 4 is a schematic flow diagram showing the air flow path of the instant invention.
Figure 4:
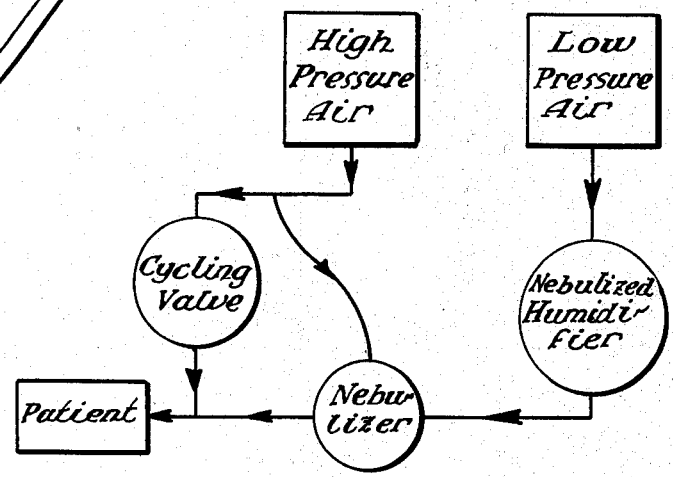

FIG. 4 shows a flow diagram with the first pressure air source feeding air into the aerosol generator with its output going into one side of the nebulizer where the air which has been humidified combines with the nebulized medicant and is fed into the mouthpiece. The high pressure air source provides high pressure air into the cycling valve. A portion of it goes to the mouthpiece area and is joined with the air received from the nebulizer.

The instant invention has been shown as being a versatile, portable apparatus for the treatment of pulmonary diseases and specifically for providing an apparatus which may be used in inhalation and exhalation therapy and medication for people having pulmonary ailments, the device being characterized by being compact, non-complex in operation and capable of handling a plurality of different inhalation therapy functions with very slight modifications of the hosing arrangements.

It should be noted that the nebulized humidity provided by the instant invention reduces the liquid particle size to under 5 microns permitting deep penetration before "rain out".

Although hose 30 and hose 32 are shown in FIG. 1 of approximately the same diameter, in the preferred embodiment, hose 30 is larger to provide a larger volume of flow.

The instant invention has been shown and described herein in what is considered to be the most practical and preferred embodiment. It is recognized, however, that departures made therefrom within the scope of the invention and that obvious modifications will occur to a person skilled in the art.

What I claim is:

1. An apparatus for pulmonary disease treatment which provides for both intermittent positive pressure breathing and medicant nebulization comprising:
a first source of pressurized fluid;
a second source of pressurized fluid, said second source having a relatively higher pressure source of fluid than said first pressure fluid source;
an aerosol generator having an inlet and an outlet, said aerosol generator connected at its inlet to the output of said first fluid pressure source;
a nebulizer for nebulizing medicant having a first inlet, a second inlet and an outlet, said first inlet being coupled to the outlet of said aerosol generator;
a pressure regulating cycling valve having an inlet and an outlet connected on its inlet side to the output of said higher second pressure fluid source;
a conduit connected at one end to said second source of pressurized fluid and at the opposite end to said nebulizer second inlet, said conduit providing pressurized fluid to nebulize a medicant disposed in said nebulizer;
apparatus outlet means connected to the outlet of said cyclic valve and the outlet of said nebulizer whereby the apparatus outlet dispenses humidified air combined with a nebulized medicant.

2. An apparatus as in claim 1, including:
a planar supporting base, said first pressurized fluid source mounted on said supporting base, said second pressurized fluid source mounted on said supporting base, and said aerosol generator mounted on said supporting base.

* * * * *